United States Patent [19]

Tsay et al.

[11] Patent Number: 4,778,755
[45] Date of Patent: Oct. 18, 1988

[54] IMMUNOASSAY METHOD

[75] Inventors: Yuh-Geng Tsay, San Jose; Susan M. Cain, Palo Alto, both of Calif.

[73] Assignee: Minnesota Mining and Manufacturing Company, St. Paul, Minn.

[21] Appl. No.: 520,921

[22] Filed: Aug. 8, 1983

[51] Int. Cl.⁴ .................. C12Q 1/54; C12Q 1/34; C12Q 1/42; C12Q 1/32; C12Q 1/00; C12N 9/99; G01N 33/535

[52] U.S. Cl. .................................... 435/14; 435/18; 435/21; 435/7; 435/4; 435/26; 435/184

[58] Field of Search .................. 435/4, 7, 18, 21, 184, 435/26, 14

[56] References Cited

U.S. PATENT DOCUMENTS

| | | | |
|---|---|---|---|
| 3,716,456 | 2/1973 | Weetall | 435/21 |
| 3,985,621 | 10/1976 | Maruyama et al. | 435/184 |
| 4,350,761 | 9/1982 | Yamamoto | 435/7 |
| 4,366,242 | 12/1982 | Neumann et al. | 435/7 |
| 4,374,925 | 2/1983 | Litman et al. | 435/7 |

FOREIGN PATENT DOCUMENTS 0075293  3/1983  European Pat. Off. ............ 435/184

OTHER PUBLICATIONS

Brauner et al., J. Immunol. Methods, 42: 375-379 (1981).
Whitaker, *Principles of Enzymology for the Food Sciences*, Marcel Dekker, Inc., New York.

Primary Examiner—Esther M. Kepplinger
Attorney, Agent, or Firm—Donald M. Sell; Philip M. Goldman

[57] ABSTRACT

In the determination of the quantity of enzyme present as a result of an immunoassay procedure, the enzyme containing component is combined with a substrate which in the presence of the enzyme yields a photometrically detectable enzymatic reaction product and a non-interfering, enzymatically inhibiting second product. The enzymatic reaction is inhibited by the addition of an inhibiting quantity of the same compound as the second product after the enzymatic reaction has continued for a time sufficient to produce photometrically detectable first products in concentrations which are a function of the quantity of enzyme present. The enzyme reaction is inhibited before the enzymatic reacton has proceeded to the point where the quantity of photometrically detectable first compound is primarily a function of the amount of substrate. This method yields a more stable test medium than methods using other enzyme inhibitors.

9 Claims, No Drawings

IMMUNOASSAY METHOD

FIELD OF THE INVENTION

This invention relates to immunoassay methods having improved reliability and convenience and to reagents therefor. In particular, this invention relates to immunoassay methods wherein the quantity of an enzyme in the system is determined by interacting the enzyme and a substrate which yields a product which can be determined using a spectrophotometer, fluorometer or the like.

BACKGROUND OF THE INVENTION

There is an increasing need to determine the presence of minute quantities of organic compounds in aqueous solutions and to quantify their concentrations. Concentrations of interest range from about $10^{-4}$–$10^{-12}$ molar and even lower. The determinations are most significant in areas of detecting the presence of drugs of abuse in physiological media, metering of therapeutic doses of drugs, and diagnosis of disease for which the presence, absence or amount of a particular organic compound is relevent to the diagnosis. Non-physiological areas of interest include investigations of water contamination, quality control and the like. Despite major advances in the immunoassay field, the precise determination of low concentrations of organic compounds continues to present problems, and many methods are very difficult to carry out in a routine manner with laboratory technicians.

DESCRIPTION OF THE PRIOR ART

Enzymatic immunological methods for identifying and quantifying organic compounds in liquids are widely used and are known as the ELISA, EIA and EMIT, for example. Basic technology for enzymatic assays and reagents therefor is disclosed in U.S. Pat. Nos. Re. 29,169 and 3,839,153, for example. A review of the current state of the art with regard to immunoassays for the detection of proteins in solutions is provided by R. Rose et al, *Manual of Clinical Immunology,* second ed. American Society for Microbiology, Washington, pp 327–429, 775–849 (1980) and by A. Voller et al, *Immunoassays for the 80's,* University Park Press, Baltimore (1981) and the publications cited therein, the entire contents of both publications being hereby incorporated by reference.

A variety of procedures have been described for stopping enzyme activity. S. Bamdad et al in *Clinical Allergy* 13, 89 (1983) describe procedures wherein IgE antibodies to food allergens are detected by ELISA, RAST and monkey PCA. S. Nakamura et al in *J. Biochem.* 64, 439 (1968) describes the inhibition of glucose oxidase with metal ions. M. Nicol et al in *J. Biol. Chem.* 24, 4292 (1966) describe substrate inhibition with glucose oxidase. W. Terpstra et al in *Biochem. Biophys. Acta.* 51, 473 (1961) describe ion sensitivity of the light reaction catalyzed by enzyme preparations from Photobacterium phosphorem. See also H. Theorell, "The Iron-Containing Enzymes B. Catalases and Peroxidases, 'Hydroperoxidases'", *The Enzymes,* Vol. II, Part I, p. 397 New York: Academic press (1951).

While the above procedures are effective to stop the enzymatic reaction, the reaction mixture is made relatively unstable by the reagents, and the photometric assay of the reaction products must be made immediately because the sensitivity degrades very rapidly after the addition of the enzyme deactivating reagent.

SUMMARY OF THE INVENTION

This invention is a method for measuring a quantity of enzyme present in a system which comprises bringing together in an aqueous medium, an enzyme and a substrate. The substrate is selected to be convertible to a photometrically detectable product in the presence of the enzyme and to yield a non-interfering, enzymatically inhibiting by-product. The enzyme and substrate are incubated for sufficient time to produce a quantity of the photometrically detectable product which is a function of the amount of enzyme present. An additional quantity of the same compound which is the enzymatically inhibiting by-product of the above reaction is then added to the aqueous medium in an amount sufficient to inhibit production of a further quantity of the photometrically detectable product. Preferably, the enzyme is an alkaline phosphatase, the substrate yields a product in the presence of the enzyme which is detectable with a fluorometer (fluorescence detection) or a spectrophotometer (colormetric determination), and the enzymatically inhibiting compound added includes phosphate ion.

DETAILED DESCRIPTION OF THE INVENTION

With immunoassays utilizing an enzymatically labeled reagent, major advantages are obtained in sensitivity because the reaction of substrate with enzyme to yield a photometrically detectable reaction product continues until the substrate is consumed. The amount of substrate which is converted is a function of the amount of enzyme present and the total time allowed for the enzymatic reaction. Each enzyme moiety may be represented proportionally in the ultimate solution by thousands of molecules of enzymatic reaction product. This provides a highly reliable amplification. This approach has been used in increasing sensitivity in both colorimetric and fluorometric detection systems.

The amount of enzymatic reaction product is a precisely related function of the amount of enzyme present only during a portion of the enzymatic reaction since the enzyme will continue to convert substrate to the corresponding reaction products until all of the substrate is exhausted. The enzyme to substrate ratio will vary widely during later portions of the reaction when the substrate concentration will be a rate determining factor. If the reaction is prolonged, the amount of enzymatic products would be a function of the amount of substrate, not a function of the amount of enzyme. As a consequence, it is critical, in carrying out enzymatic immunoassays, that the photometric measurements are made at a precise time after the enzyme and substrate are initially contacted. While the precise time can be selected over a wide range, the times must correspond exactly for the sample and control, and prolonged delay in making the measurements will reduce sensitivity or even invalidate the results. It is, therefore, an object of this invention to provide a method which can be used in enzymatic immunoassays to instantly stop an enzymatic reaction, which can be used after passage of a selected amount of time, and which yields a reaction mixture which is photometrically stable over an extended period of time.

A wide variety of enzymatic immunoassays have been developed, and in general, enzymatic immunoassays are well-known procedures in the art for detecting a wide variety of organic compounds. Examples of enzymatic immunoassays include sandwich immunoassays, inhibitions assays, competitive assays, and sandwich assays, all of which are described in detail by A. Voller et al, "Enzyme-Linked Immunosorbent Assay", in *Manual of Clinical Immunology*, supra, pp. 359–371 and the references cited therein.

In one method, an antigen on an insoluble support is contacted with a test sample containing antibody to be detected, the support is washed, enzyme labeled-antibody is contacted therewith and incubated, the excess is removed, and enzyme substrate is added and incubated. The rate of substrate degradation, indicated by the color change, is proportional to the antibody concentration in the test samples. In a corresponding competitive assay, the antigen attached to an insoluble support is contacted with the sample containing antigen-specific antibody and an enzyme-labeled antigen-specific antibody, the two antibody forms competing for conjugation with the antigen. After incubation, excess is removed, the solid phase washed, enzyme substrate added, and the enzymatic reaction product is detected.

In assays for antigens and haptens, the antibody specific for the antigen or hapten is bound to an insoluble support, and this support is contacted with a test sample containing the target antigen and an enzyme-labeled conjugate of the target antigen. After incubation, the liquid phase is separated, and the solid phase is washed and contacted with enzym substrate.

In the double antibody sandwich method, a first antibody specific for antigen or hapten is bound to a solid support, and the support is incubated with the test sample containing the target antigen. The support is separated from the sample, washed, and contacted with a second antigen-specific antibody which reacts with a different epitope or antigen site of the antigen. The second antibody, if unlabeled, can be subsequently bound with an enzyme-labeled anti-(second antibody)antibody (i.e., anti-species globulin). Enzyme substrate can then be added and the reaction products determined. In an inhibition assay method, reference antigen linked to a solid support is contacted with enzyme-labeled antigen-specific antibody and with the test sample thought to contain the antigen. After incubation, the liquid phase is separated, and the solid phase is washed. Enzyme substrate is then added. The difference in substrate degradation between the tests with the reference conjugate alone and with the conjugate plus test sample is proportional to the amount of antigen in the test sample. Double sandwich immunoassays such as ELISA have become very popular and are used to measure concentrations of organic compounds having a wide variety of sizes and chemical characteristics.

Fluorometric immunoassays of the type involved in the present invention are basically enzymatic immunoassays in which fluorometry is employed to measure the amount of enzyme present in a system. In general, a substrate which does not have fluorescent activity, upon combination with an enzyme in an aqueous medium, yields an enzymatic reaction product which is fluorescent and which can be detected by means of a fluorometer. In ELISA assays, the substrate is converted to yield a chromophor which can be determined at a characteristic frequency with a standard spectrophotometer. In the fluorescent variant, the sample upon exposure to light at an excitation frequency, emits a fluorescent light having a characteristic emission frequency, the light intensity being a function of the amount of fluorescent compound in the sample.

Both colorimetric and fluorescent approaches have been applied in homogeneous immunoassays as well as in the solid phase immunoassays described above.

The equipment employed in measuring levels of fluorescence include fluorometers available from Perkin-Elmer, American Instrument Company, and Turner Designs. The ALLERGENETICS FLUORO-FAST TM fluorometer (Allergenetics, Inc., Mountain View, Calif.) is preferred. For colorimetric immunoassays, a wide variety of available spectrophotometric instruments can be employed. In particular, spectrophotometers are available from Beckman Instruments, Perkin-Elmer, Varian Associates and Gilford.

The method of this invention comprises taking an enzyme solution, a sample containing enzyme which has been produced by an immunoassay sequence, and determining the amount of enzyme present in the sample. The method of this invention can be used with enzyme solutions which have been obtained using any immunoassay procedure, including but not limited, to those described above. In the method of this invention, the quantity of enzyme present in a system is measured by interacting it with substrate. The enzyme and the substrate are brought together in an aqueous medium. The substrate in the presence of the enzyme must be convertable to a photometrically detectable (first compound) and a non-interfering, enzymatically inhibiting (second compound). This reaction is continued for a sufficient time to produce an amount of the first compound which is a function of the amount of enzyme present, but less than the time required for the amount of the first compound to be a function of the amount of substrate present.

The term "photometrically detectable first compound", as used herein, refers to a product which is a chromophor or fluorophor, that is, which can be determined by spectrophotometric or fluorescent procedures, respectively. The term "non-interfering, enzymatically inhibiting second compound", as used herein, refers to an enzymatic reaction compound which is a product of the enzymatic reaction; which is different from the photometrically detectible first compound; which, if it has photometric properties, is clearly photometrically distinguishable from a photometrically detectable first product (absorbs and/or emits at different light frequencies); and which, if present in sufficient quantity in solution, inhibits enzymatic activity of the enzyme-substrate reaction.

The enzymes to be measured in this procedure are present as enzyme labels conjugated to hapten, antigen or antibody moieties. In heterogeneous immunoassays, the enzyme-labeled compounds can be present on an insoluble support which has been separated from samples and reagent solutions, or the enzyme-labeled compounds can be present in a solution which has been separated from an insoluble support. In homogeneous immunoassays, the enzyme-labeled compounds are usually present together with the sample and reagents.

This method is suitable for use with all compounds and materials which are conjugated to enzymes and is not limited to any specific class of compounds which have been heretofore conjugated to enzymes. Furthermore, the method of this invention can be used with all enzyme labels which, when interacting with an appropriate substrate, yield photometrically detectable first products and non-interfering, enzymatically inhibiting second products.

The types of enzymes which can be used to provide colorimetrically and fluorometrically detectable enzymatic reaction products are described by Hawk et al., *Practical Physiological Chemistry*, McGraw Hill; New York, pp 306-307, (1954), and U.S. Pat. Nos. 4,190,496 and 4,299,916, the entire contents of which are hereby incorporated by reference. In the presence of an alkaline phosphatase, for example, the substrate p-nitrophenyl phosphate is converted to the yellow chromophor p-nitrophenol and the by-product (inhibitor) phosphate ion. The substrate 4-methylumbelliferylbeta-D-galactoside in the presence of the enzyme beta-D-galactosidase yields the fluorophor 4-methylumbelliferone and the by-product (inhibitor) D-galactose. The enzyme glucose-6-P dehydrogenase converts the substrate glucose-6-P to the chromophor NADH and the by-product (inhibitor) D-glucon-delta-lactone-6-phosphate. A preferred system includes the enzyme alkaline phosphatase and substrate 4-methylumbelliferyl phosphate which yields a fluorophor 4-methylumbelliferone and by-product (inhibitor) phosphate ion.

Other examples of suitable enzyme labeling agents and compounds with which they are conjugated, coupling procedures and substrate reactions are disclosed in U.S. Pat. Nos. 4,214,048, 4,312,943 and 4,302,438, the entire contents of which are hereby incorporated by reference.

Fluorogenic enzymes (enzymes in the presence of which a substrate will produce a fluorescent product) are preferred labeling moieties. Methods for bonding enzymes to antibodies without impairing the ability of the antibody to selectively conjugate with antigen are well-known in the art. Suitable enzymes and procedures for coupling them to antibodies are described in U.S. Pat. No. 4,190,496, The preferred fluorogenic enzymes and the suitable substrates corresponding thereto are alkaline phosphatase and 4-methylumbelliferyl phosphate, and beta-D-galactosidase and 4-methylumbelliferyl-beta-D-galactoside. Fluorescent labeled reagents can be prepared from standard fluorescent moieties known in the art and described above. Other procedures are described in commonly assigned, copending application Ser. No. 489,897 filed Apr. 29, 1983 entitled "Fluorometric Assay of Chymopapain and Reagents Therefor".

The substrate solution is incubated with the enzyme for a sufficient time for the fluorescent or colorimetric reaction product to form. At temperatures of from 18° to 40° C., incubation times of 5 to 240 minutes can be used. Preferably, the temperature is within the range of from 20° to 26° C., and the incubation time is from 30 to 90 minutes. In any event, incubation is continued until the amount of fluorescent or colorimetric enzymatic reaction product is still in the range of concentrations which are a function of the amount of enzyme of the solution, but not so long as to yield concentrations which are primarily a function of the amount of substrate present.

The second step in the process of this invention comprises adding an inhibiting quantity of the noninterfering enzymatically inhibiting second enzymatic reaction product. The inhibiting quantity is the amount which is sufficient to inhibit production of a significant further quantity of the photometrically detectable first product.

Examples of enzymes, substrates, photometrically detectable first products and non-interfering, enzymatically inhibiting second products are described above. In general, the enzyme inhibiter listed is added to the mixture when sufficient enzymatic reaction has occurred in a quantity which is sufficient to stop further enzymatic activity.

In a preferred system wherein the enzyme label is an alkaline phosphatase and the substrate is 4-methylumbelliferyl phosphate, the photometrically detectible enzymatic reaction product is 4-methylumbelliferone and the non-interferring, enzyme inhibiting by-product is phosphate ion. Therefore, addition of sufficient further phosphate ions, preferably in an aqueous phosphate buffer solution, to provide at least a 0.003M phosphate solution and preferably at least a 0.18M phosphate solution substantially terminates further enzymatic activity. Furthermore, the reaction mixture is stable and can be stored for an extended period of time at temperatures within the range of from 4° to 26° C. without significant change in the level of photometrically detectible compound.

Thereafter, the photometric measurement can be made within 72 hours after the enzymatic reaction is stopped if the solution is stored at suitable temperatures.

This invention is further illustrated by the following specific but non-limiting examples. Temperatures are given in degrees Centigrade and concentrations as weight percents unless otherwise specified.

EXAMPLE 1

Microwells to which a BSA conjugate of perennial ryegrass pollen allergen is adhered are rinsed for 5 minutes with a buffered rinse solution containing 0.85 wt. % sodium chloride, 0.05 wt. % TRITON X405 non-ionic surfactant (Rohm and Haas), 0.01 wt. % BSA, and 0.1 wt. % sodium azide preservative in a 0.01 aqueous phosphate buffer solution, pH 7.2, and the surplus rinse solution is removed. The microwells are then contacted with patient serum containing perennial ryegrass pollen allergen specific IgE and incubated for 2 hrs. The serum is removed, and the wells are washed three times with the buffered rinse solution.

The buffered rinse solution is prepared by diluting the following concentrate with 50 parts by volume of distilled or deionized water to one part by volume of concentrate:

| | |
|---|---|
| Bovine serum albumin (BSA) | 0.5 wt. % |
| Non-ionic surfactant (TRITON X-405) | 0.1 wt. % |
| Sodium Chloride | 17 wt. % |
| Sodium azide | 2 wt. % |
| Sodium phosphate | 0.05 M |
| pH adjusted to | 7.4 |

Serum IgE specific antibody for perennial ryegrass pollen allergen is conjugated to the microwell surfaces.

The microwells are then contacted with 100 micoliters of a solution of alkaline phosphatase conjugated anti-human IgE monoclonal antibody prepared according to a modified procedure of M. O'Sullivan, et al., *Analytical Biochem.*, vol. 100, page 100 (1979). The monoclonal antibody is applied in a solution of 0.01M phosphate buffered saline, pH 7.2, containing 4 wt. % polyethylene glycol having a molecular weight of 4000 (PEG 4000), 0.05 wt. % TRITON X-405, 0.01 wt. % BSA, and 0.1 wt. % sodium azide preservative. The alkaline phosphatase conjugated anti-human IgE monoclonal antibody solution is removed from the microwells, and they are rinsed three times with the buffered rinse solution described above.

To each of the microwells is then added 100 microliters of a substrate solution containing $10^{-4}$M 2-amino-2-methyl-propanol, pH 9.5 in deionized water containing 0.125 mM magnesium chloride and 0.1 wt. % sodium azide. After 45 minutes, the fluorescence level in one group of wells (Set A) is read with a fluorometer with the excitation at 365 nm and the reading at 450 nm. To a second group of wells (Set B) is added 50 microliters of 0.5M phosphate buffer solution, pH 9.5 containing 0.1 mM EDTA, and the solution is maintained at 20° C. for 18 hours before reading. No phosphate buffer solution is added to a third group of wells (Set C), and they are maintained at 20° C. for 2 hours before reading. By comparing the reading with levels measured by repeating the procedure with control solutions having known concentrations of serum specific IgE for perennial ryegrass allergen, the procedure for determining the serum specific IgE levels in the patient serum is completed.

TABLE A

| Set | specific IgE conc. | Incubation Time | F.U. |
|---|---|---|---|
| A | .1 IU/ml | 45 min. | 103 |
|  | .8 | 45 min. | 263 |
|  | 4 | 45 min. | 578 |
|  | 20 | 45 min. | 1187 |
| B | .1 IU/ml | 18 hrs. | 123 |
|  | .8 | 18 hrs. | 322 |
|  | 4 | 18 hrs. | 710 |
|  | 20 | 18 hrs. | 1426 |
| C | .1 IU/ml | 18 hrs. | 2952 |
|  | .8 | 18 hrs. | off scale |
|  | 4 | 18 hrs. | off scale |
|  | 20 | 18 hrs. | off scale |

As can be seen from Table A, the level of fluorescence in the Set B of wells was essentially the same as those measured in the Set A wells, showing relative stability in the amount of fluorescent enzymatic reaction product in the sample deposit storage for 18 hours at 20° C.

In Set C wells, enzymatic activity continued, and readings made therewith had greatly reduced sensitivity.

We claim:

1. A method for measuring a quantity of an enzyme present in a system comprising
    (a) bringing together, in an aqueous medium, the enzyme and a substrate, which in the presence of the enzyme is converted to a photometrically detectable first compound and a second product for a time sufficient to produce a quantity of the first compound which is a function of the amount of enzyme present,
    (b) then adding additional second product to the aqueous medium in an amount sufficient to substantially terminate further enzymatic reaction, and
    (c) determining the quantity of the first compound as a function of the amount of enzyme present.

2. A method for measuring a quantity of an enzyme present in a system comprising
    (a) bringing together, in an aqueous medium, the enzyme and a substrate, which in the presence of the enzyme is converted to a photometrically detectable first compound and a second product for a time sufficient to produce a quantity of the first compound which is a function of the amount of enzyme present,
    (b) then adding additional second product to the aqueous medium in an amount sufficient to substantially terminate further enzymatic reaction, and
    (c) determining the quantity of the first compound as a function of the amount of enzyme present,
    wherein the enzyme is an alkaline phosphatase, the substrate yields a fluorescent product in the presence of the enzyme, and the second product includes phosphate ion.

3. The method of claim 2 wherein the substrate is 4-methyl-umbelliferyl phosphate, and phosphate ion is added as a phosphate solution having a pH of from 8.15 to 10.10 and containing sufficient phosphate ion to substantially terminate further enzymatic reaction.

4. A method for measuring a quantity of an enzyme present in a system comprising
    (a) bringing together, in an aqueous medium, the enzyme and a substrate, which in the presence of the enzyme is converted to a photometrically detectable first compound and a second product for a time sufficient to produce a quantity of the first compound which is a function of the amount of enzyme present,
    (b) then adding additional second product to the aqueous medium in an amount sufficient to substantially terminate further enzymatic reaction, and
    (c) determining the quantity of the first compound as a function of the amount of enzyme present,
    wherein the enzyme is an alkaline phosphatase, the substrate yields a chromophor product in the presence of enzyme, and the second product includes phosphate ion.

5. The method of claim 4 wherein the substrate is p-nitrophenyl phosphate, and phosphate ion is added as a phosphate solution having a pH of from 8.5 to 10.0 and containing sufficient phosphate ion to substantially terminate further enzymatic reaction.

6. A method for measuring a quantity of an enzyme present in a system comprising
    (a) bringing together, in an aqueous medium, the enzyme and a substrate, which in the presence of the enzyme is converted to a photometrically detectable first compound and a second product for a time sufficient to produce a quantity of the first compound which is a function of the amount of enzyme present,
    (b) then adding additional second product to the aqueous medium in an amount sufficient to substantially terminate further enzymatic reaction, and
    (c) determining the quantity of the first compound as a function of the amount of enzyme present,
    wherein the enzyme is a beta-D-galactosidase, the substrate yields a fluorescent product in the presence of the enzyme, and the second product includes D-galactose.

7. The method of claim 6 wherein the substrate is 4-methylumbelliferyl-beta-D-galactoside, and a solution of D-galactose is added in quantity sufficient to substantially terminate further enzymatic action.

8. A method for measuring a quantity of an enzyme present in a system comprising
    (a) bringing together, in an aqueous medium, the enzyme and a substrate, which in the presence of the enzyme is converted to a photometrically detectable first compound and a second product for a time sufficient to produce a quantity of the first compound which is a function of the amount of enzyme present, (b) then adding additional second product to the aqueous medium in an amount sufficient to substantially terminate further enzymatic reaction, and (c) determining the quantity of the first compound as a function of the amount of enzyme present, wherein the enzyme is a glucose-6-P-dehydrogenase, the substrate yields a fluorescent product in the presence of the enzyme, and the second product includes D-glucon-delta-lactone-6-phosphate.

9. The method of claim 8 wherein the substrate is glucose-6-P and a solution of D-glucon-delta-lactone-6-phosphate is added in a quantity sufficient to substantially terminate further enzymatic action.

* * * * *